United States Patent [19]

Ross

[11] 4,017,820

[45] Apr. 12, 1977

[54] HUMIDITY SENSOR WITH MULTIPLE ELECTRODE LAYERS SEPARATED BY A POROUS MONOLITHIC CERAMIC DIELECTRIC STRUCTURE

[75] Inventor: Bernd Ross, San Diego, Calif.

[73] Assignee: Illinois Tool Works Inc., Chicago, Ill.

[22] Filed: May 13, 1976

[21] Appl. No.: 685,837

Related U.S. Application Data

[63] Continuation-in-part of Ser. No. 599,196, July 25, 1975, abandoned.

[52] U.S. Cl. .................................. 338/35; 338/325
[51] Int. Cl.[2] ......................................... H01L 7/00
[58] Field of Search .............. 338/35, 34, 314, 325;
200/61.04, 61.06; 73/336.5, 73; 340/235, 232
E; 23/254 E, 255 E; 324/65 R, 65 P;
29/610–612; 261/129

[56] References Cited

UNITED STATES PATENTS

| | | | |
|---|---|---|---|
| 3,255,324 | 6/1966 | Ovshinsky | 338/34 X |
| 3,916,367 | 10/1975 | Nicholas et al. | 338/35 |

Primary Examiner—C. L. Albritton
Attorney, Agent, or Firm—Glenn W. Bowen; Robert W. Beart

[57] ABSTRACT

The invention concerns a humidity or moisture sensor, with a relatively thick sensitive monolithic ceramic volume. The sensitive volume is defined by a porous ceramic material with multiple electrodes buried therein in parallel planes which extend substantially entirely across two dimensions of the structure. Moisture entering the porous crystalline matrix is subjected to a high electric field giving rise to a current which is a function of the ambient moisture. By virtue of the inert ceramic surface and the buried precious metal electrodes, the device is sensitive, fast, yet electrically, chemically, thermally and mechanically stable.

2 Claims, 7 Drawing Figures

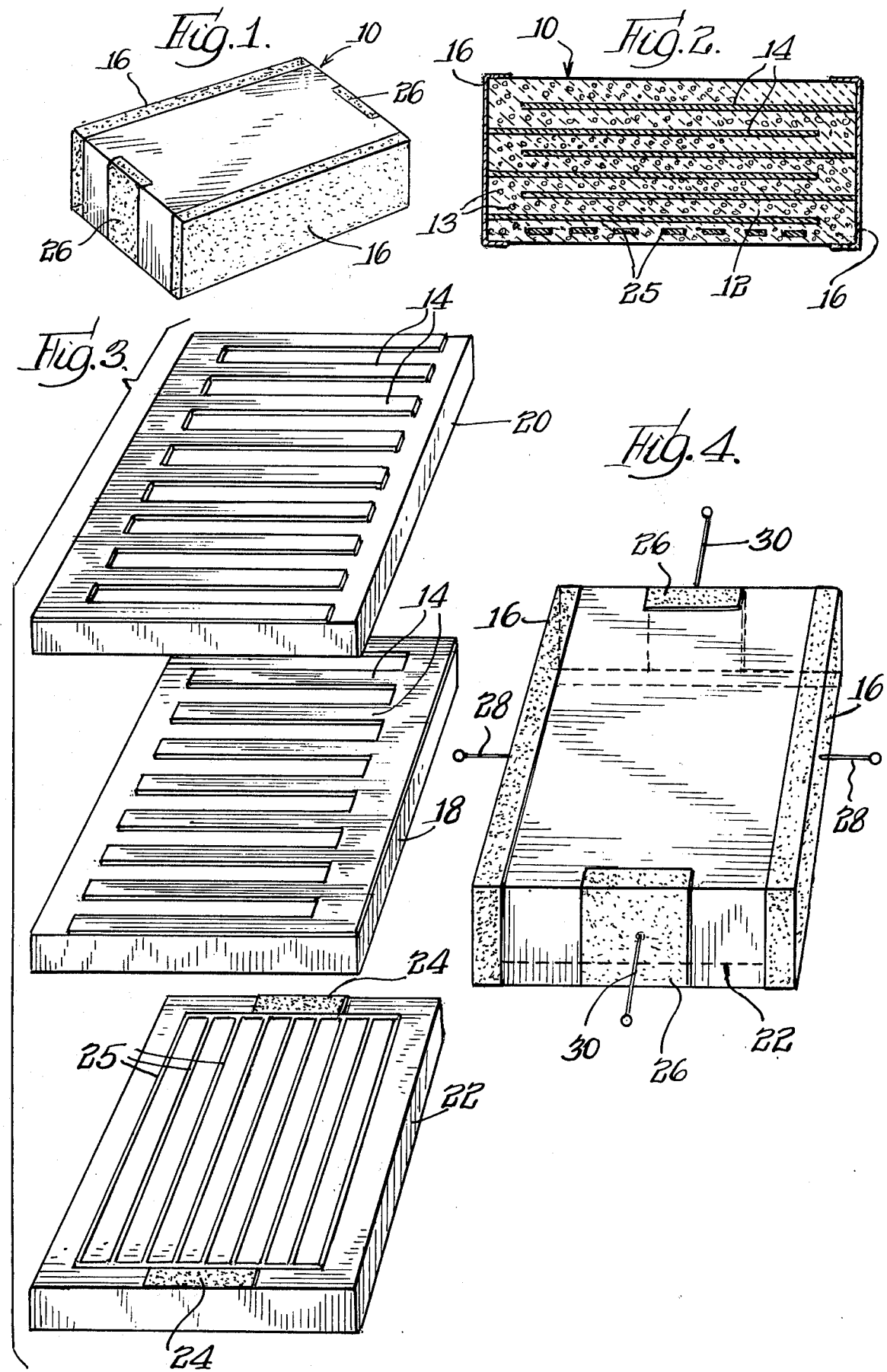

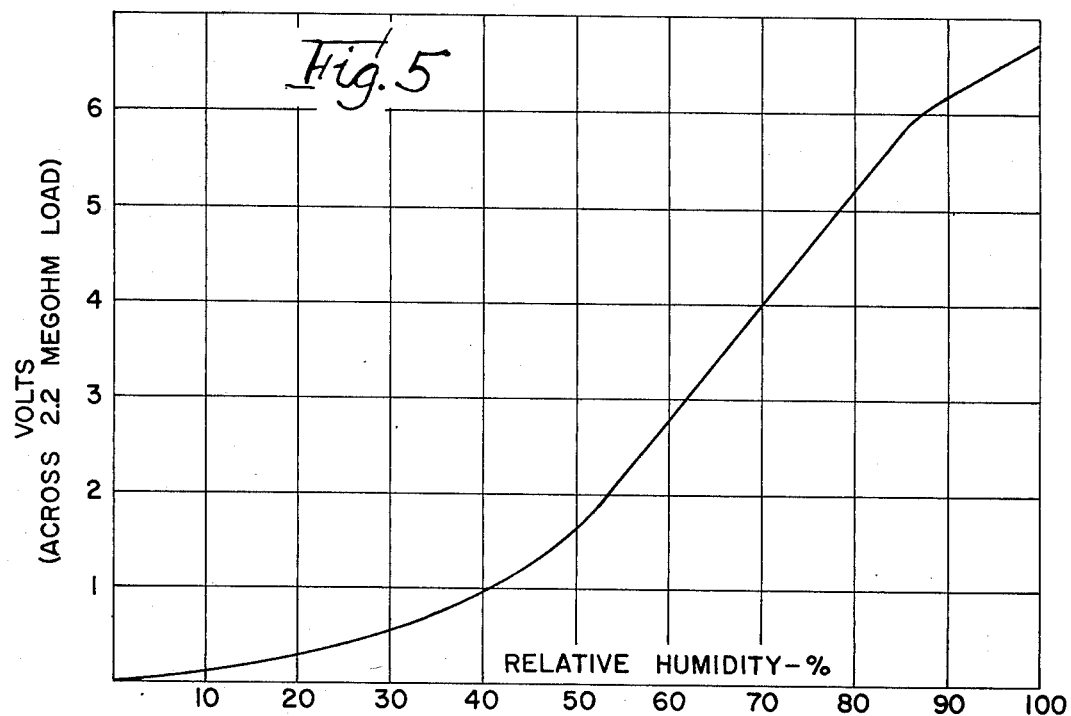
Fig. 5
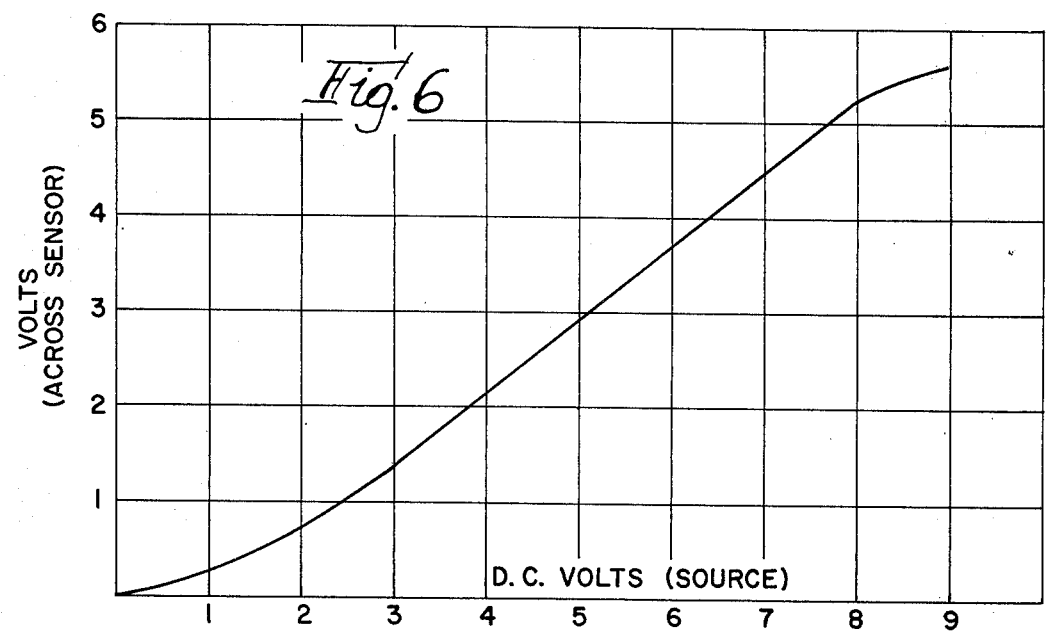
Fig. 6
Fig. 7
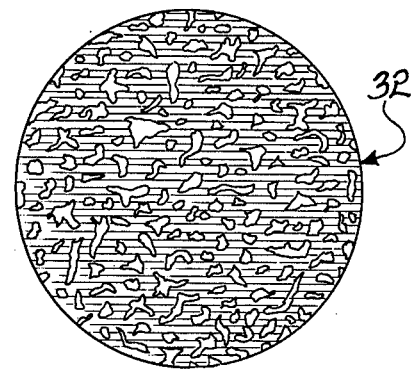

HUMIDITY SENSOR WITH MULTIPLE ELECTRODE LAYERS SEPARATED BY A POROUS MONOLITHIC CERAMIC DIELECTRIC STRUCTURE

BACKGROUND OF THE INVENTION

This application is a continuation-in-part of United States Ser. No. 599,196, filed July 25, 1975, now abandoned.

Numerous prior humidity sensing devices have been proposed which utilize a hygroscopic substance, such as an ionic salt, which is applied to a surface that lies between two conductive electrodes. Another prior type of humidity sensing device employed a porous structure which is impregnated with a hygroscopic substance. A third type of prior humidity sensing device is the surface resistivity type, which relies on absorbed water between electrodes.

The first mentioned type of humidity sensor is slow to respond and may be easily damaged and is subject to contamination. The impregnated salt will be leached out of the second type of humidity sensor over a period of time when it is exposed to relatively high humidity, thus resulting in an inoperative or ineffective sensor. This type of sensor also is slow to respond and has poor hysteresis and drift characteristics. The third type of humidity sensor that was mentioned above also is unacceptable for many applications because it requires special measuring circuits due to the high surface resistivity of the insulating substrate. Thus, there has been a need for sometime for a low-cost, extremely sensitive humidity sensor with a fast response time that has a minimum of hysteresis or drift.

The advantages of the disclosed invention over prior art devices are high sensitivity coupled with small physical size, good stability, ruggedness and low cost. The sensitivity is best illustrated by FIG. 5 showing the output voltage of a sensor of subject invention plotted against relative humidity. The sensor of FIG. 5 is a chip which may have dimensions of 0.280 × 0.236 × 0.015.

The technology underlying the disclosed humidity sensor is that of thick film circuit fabrication. This technique is widely used in the fabrication of electronic circuits and components, such as ceramic capacitors, for communication, electronic data processing, and instrumentation for measurement. It is based upon the application of a conductive metal ink upon a green or fired ceramic substrate acting as a dielectric. The process of fabrication for the subject invention utilizes a precious metal ink, screened through a suitable mask, usually a silk screen, upon a thin wafer of green ceramic material held together by an appropriate resinous binder agent. The wafers with the metal ink electrode patterns are stacked together, pressed and cut into individual green sensor chips. These are placed in an oven for a drying cycle to remove the resinous binder without disturbing the dielectric-electrode structure. The dried chips are sintered in a subsequent firing cycle during which the ceramic dielectric and the electrode metal grains are bonded and densified. The degree to which this maturation process is allowed to progress is measured by the dimensional shrinkage of the chips and the electrical parameters of the resulting components. Volume shrinkage of a chip of the subject invention to complete maturity is approximately 38%.

It is an important object of this invention to carefully control the shrinkage of the fired ceramic dielectric so that it proceeds to between 10 and 50% with the optimum being between 25 and 45%, depending upon the particular ceramic composition involved.

The degree of maturation of the ceramic can be controlled in various ways. One such method involves the control of the temperature while keeping the firing time constant. Thus, if one desires a specific porosity, one may reduce the firing temperature to a temperature, for example, corresponding to 85 to 95% of the maturation firing temperature, while holding the duration of the firing cycle constant. The maturation firing temperature is here defined as the most convenient temperature at which maximum shrinkage of the ceramic part occurs, with a minimum amount of residual porosity. Similarly, one could shorten the corresponding duration of the firing cycle by 30 to 50% while holding the firing temperature constant. Alternately, the firing temperature may be reduced and the duration of the firing cycle may be shortened correspondingly.

The porous multi-layered ceramic humidity sensor that is manufactured in this manner has an extremely high sensitivity and a very fast response time, due to the closely spaced multiple electrode layers that extend substantially entirely across two dimensions of the structure and are buried into the monolithic dielectric chip since a relatively high electric field is produced between each pair of electrode layers because of their close spacings.

After the firing cycle, the electrodes of the present invention which intercept the edges of the chips are provided with external metal terminals so that opposed sets of electrodes are electrically connected in parallel and are conveniently available for interconnection with external apparatus.

DESCRIPTION OF THE DRAWINGS

The present invention is illustrated by reference to the drawings in which:

FIG. 1 is a top plan view of a multi-layered humidity sensor constructed in accordance with the present invention;

FIG. 2 is a sectional view taken through the center of the humidity sensor of FIG. 1;

FIG. 3 is an exploded perspective view showing the electric field-producing layers and the heating electrode of the humidity sensor of FIG. 1;

FIG. 4 is a perspective view of a complete humidity sensor, with leads attached thereto, which is constructed with a heater included therein;

FIG. 5 is a characteristic curve giving signal voltage output across a 2.2 megohm load plotted along the ordinate versus relative humidity percentage as the abscissa at a constant 9 volts applied voltage;

FIG. 6 is a graph plotting signal voltage as the ordinate against voltage applied to the sensor as the abscissa at a constant relative humidity of approximately 80%; and FIG. 7 is a greatly enlarged view of the electrode structure which shows its lacy network configuration.

TECHNICAL DESCRIPTION OF THE INVENTION

The humidity sensors of the present invention may be manufactured by a process such as described below. This process utilizes various ceramic powder mixtures, some of which may be purchased directly from suppliers, which have various amounts and types of additives added to them, including a solvent, a binder, a lubricant and a plasticizer, etc. The ingredients are initially milled in a ball mill to obtain thorough mixing. After the mixture is milled, the resulting slurry is put into a supply tank, and it is then supplied to a tape casting container which is positioned over a moving carrier tape material such as polyethylene, or other suitable plastic material. A doctor blade is positioned over the opening and the thickness of the slurry is controlled by adjusting the height of the blade. Additional control of the cast slurry thickness is afforded by controlling the speed of the carrier tape and the viscosity of the slurry.

The cast tape is next allowed to air-dry, or, if desired, drying may be achieved by blowing dry hot air over the tape. The dried tape now carries the ceramic layer which is in its green, or uncured, state. The ceramic layer is next peeled from the carrier tape. Electrode layers are deposited onto the ceramic layers by silk-screening, vapor deposition or other suitable method. The layers are then stacked and compressed together to form the desired multi-layered structure.

The structure is now ready for firing to maturation in a sintering furnace. The multi-layered structure is heated in a sintering oven at a predetermined temperature for a predetermined time in order to mature the ceramic dielectric material to a desired state of density, such that a porous structure of at least a ten percent open cell construction results.

Various material compositions have been utilized in the construction of the subject sensor and their properties may be tailored to the specific characteristics desired. For example, one may minimize the influence of ambient temperature by selecting a composition whose temperature coefficient and dielectric constant are very small, so that the sole temperature effect is that governing ionic motion of the hydrogen and hydroxyl ions. Other compositions can minimize or maximize the electrical capacitance of the device to achieve certain circuit effects, for example, a humidity controlled oscillator. By employing different compositions of ceramics in the same size chip capacitance has been varied between 200 pf and 2000 pf. Compositions may contain barium titanate, bismuth titanate, calcium titanate, cerium titanate and other types of materials.

One suitable composition for constructing the humidity sensor of the present invention may be formed by using a mixture which has previously been used to construct ceramic chip capacitors comprising the following ingredients:

| | |
|---|---|
| Magnesium titanate ($MgTiO_3$) | 65%–75% by weight |
| Zinc oxide (ZnO) | 10%–20% by weight |
| Calcium titanate ($CaTiO_3$) | 4%–7% by weight |
| Titanium dioxide ($TiO_2$) | 6%–9% by weight. |

The preferred material for the sensor of the present invention is pure cerium titanate. The powder is made by combining cerium oxide and titanate oxide in stoichiometric ratio (2 moles $CeO_2$ to 3 moles $TiO_2$). This material is mixed by milling and blending and it is then calcined at 1050° to 1200° C., preferably at 1150° C. The calcined material is crushed in a mortar and pestle, or put through a jaw crusher, until it attains a grain size small enough to pass a No. 16 mesh screen. The preparation of the material itself is thus somewhat similar to that of the Mayer U.S. Pat. No. 2,862,090 but the layered electrode construction of the present invention differs substantially from the surface electrode construction of the device of the Mayer patent, and this addition leads to the decided advantage of the present invention.

The multi-layer construction of FIGS. 1–4 is then obtained by printing on the electrodes, stacking the printed layers so that the electrodes are stacked in parallel planes and the structure is then dried, fired, and electrode terminations are formed as before. The firing temperatures preferably range from 1120° to 1220° C. for one hour. Other firing temperatures and times may, of course, be utilized to achieve the desired porous structure. Best results have been achieved with an electrode ink printed in comb patterns, and the resulting structure fired at 1175° C. for 1 hour. Fresh units could then be measured with a load resistance of only 1000 ohms, however, material printed with three part ink comprising gold, platinum, palladium also gives good results.

To minimize degradation, the units may be stabilized by dipping them into an aqueous solution of polyethylene glycol 400, 0.5 to 10% with optimum being at 1 to 2%. The resulting units have an improved resistance to degradation by a factor of at least 100.

The humidity sensor of the present invention is shown in FIGS. 1 and 2, in which the reference number 10 indicated the sensor generally. The sensor 10 includes a homogeneous monolithic dielectric structure initially formed of dielectric layers 12 with the electrode layers 14 being buried therein. The electrode layers 14 may be rectangular or square electrode areas, if desired, and they extend in substantially parallel planes substantially entirely across the two dimensions of each plane to form a three-dimensional sensing structure. The comb-like structure shown in FIG. 3 is ferred. The electrode layers 14 may be deposited by silk screening, vapor deposition or other suitable method, as previously mentioned, and are preferably formed of precious metal containing one or more of platinum, gold, palladium, osmium, iridium or rhenium. The comb-like fingers of the electrode on the dielectric layer 18 are preferably aligned with the comb-like fingers of the electrode on the dielectric 20, that lies immediately adjacent it. The dielectric layers 18, 20 have numerous pores, or open cells, after firing to maturation. These are represented schematically by the number 13 of FIG. 2 and the exact configuration is best seen with the aid of a scanning electron microscope.

A pair of conductive terminal coating 16 are applied to the ends of the sensor 10 to electrically connect the offset electrode layers 14 on opposite edges of the sensor. A conductive electrode heater may be provided on a separate dielectric layer 22 which has a pair of conductive terminal areas 24 on opposite edges of the device and conductive bars 25 that run between the two terminal areas 24. When the layer 22 is included in the sensor 10, a second pair of conductive terminal coatings 26 are applied to the sides of the sensor 10 in order to provide for electrical connections to the terminal areas 24. Electrical current that passes through the terminal areas 24 and the bars 25 then heats the humidity sensor. Electrical connections to external circuitry is made to the terminals 16 through the leads 28 and to the terminals 26, through the leads 30.

An important objective of this invention is to choose ceramic ingredients as well as metal electrode ingredients such that they exhibit chemical stability in their final form. If ordinary metals were employed in the electrode structure, they would soon go into ionic solution amongst the water molecules, and would be ionically transported across the crystalline matrix comprising the dielectric. This would lead to an instability exhibited variously as polarization, hysteresis or long term drift and would eventually reduce the impedance of the device. A similar process would pertain to the ingredients of the dielectric if they are poorly chosen.

For this reason, the electrode materials are chosen from the group of precious metals; platinum, gold and palladium or combinations thereof. Since metals and oxides are co-sintered at high temperatures, the storage temperature for the chips may also be quite high without possibility of sensor damage. The electrodes formed by the described thick film manufacturing process provide a lacy interconnected open network 32, a portion of which is shown in FIG. 7, due to the more rapid sintering of metal particles relative to the ceramic dielectric and to the influence of surface tension on the sintered metal structure. Thus, water vapor can readily diffuse even through solid plate-like electrode networks and the resetting response time may approach that of the comb electrode structure.

While the sensor of FIG. 3 has a very rapid response, its response speed may be increased by adding a heater element to the structure. This element is usually placed underneath the electrodes. The heater has the function to increase the diffusion rate of vapor molecules within the ceramic porous volume to bring the sensor into equilibrium with its environment more rapidly. It is fabricated by a screening technique similar to the one used in providing the electrode structure.

The operation of the device is believed to be as described below it being understood that the invention is not limited by the theory proposed to describe its operation. Moisture enters the open polycrystalline matrix of the ceramic chip. On the basis of electronmicroscopy it has been established that the optimum average grain size is about 0.5 to 1 micron. The water molecules are absorbed by the large surface area comprising the dielectric crystallites. The catalytic nature of the crystallite surface coupled with the relatively high electric field between the electrodes (on the order of 1000 volts/cm) ionizes the moisture. These ions can then provide an electric current between electrodes. This current provides the output signal and simultaneously removes the water molecules making the detector ready for further humidity measurement. The graph of FIG. 5 supports this model since the voltage intercept along the abscissa gives a value close to the electrochemical potential for the dissociation of water (1.229 eV). While the sensor can be operated at a voltage below this value, it is desirable to use larger applied voltage magnitudes to obtain more stable and dependable operation.

The material for the heater is preferably pure platinum in order to withstand high local temperatures during instantaneous spot heating. However, other metals may be used.

The operation of the heater is either continuous (during and between measurements) or pulsed (between measurements only). Its purpose is to allow rapid outgassing of the porous structure, allowing a more rapid return to measurement equilibrium.

By reference to FIG. 5, it may be seen that the central portion of the curve contains a segment in which the voltage is substantially linear with respect to the relative humidity. There are linearizing networks, using, for instance, an operational amplifier, which allow extending the range of linear operation of the sensor over a wider humidity range.

To minimize the effect of the sensor's shunting capacity which is a factor at low humidity with 1000 Hz A.C. voltage applied, a shunting capacitor may be employed as part of the load. The capacitance may be chosen to have approximately twenty times the value of the sensor capacitance, a load shunt of 0.47 uf gave good results.

While control of the time-temperature product is a convenient way of making a porous ceramic structure, other types of porous structures may be utilized for the dielectric material, and, in addition, other ways of making a ceramic structure porous may be undertaken. For example, a presintered ceramic block could be crushed and then resintered in order to obtain a coarser and, thus, a more porous structure. Another way of obtaining a porous ceramic structure is to incorporate a fugitive material, such as carbon, into the dielectric so that during maturation the fugitive material will be released from the structure while creating porous voids in the process.

While a porous ceramic material is preferred for the dielectric of the humidity sensor, it is apparent that various other porous dielectric materials which allow for a plurality of closely spaced electrode layers may alternately be employed.

As typical values the electrode thickness may be between 0.0001 and 0.0005 inch. The thickness of the dielectric between electrodes may be between 0.0005 and 0.0005 inch. The electrodes are preferably entirely buried in the monolithic porous dielectric with only the edge showing at the end of the structure which eventually forms a part of the termination. The thickness of ceramic and electrode layers that must be traversed by incoming water molecules to result in detection will then be about 0.0015 inch, and the thickness of the total detection volume will be from 0.005 to 0.010 inch.

In the present invention, a homogeneous monolithic dielectric structure is formed which has no interfaces in it, such as occur in Ovshinsky U.S. Pat. No. 3,255,324, between the moisture responsive composition and the impervious insulating sheet. The ceramic thick film technology construction of the present invention allows stacking of electrodes such that the distance between electrodes of 0.001 to 0.002 inch are routinely achieved without fear of electrical shorting. The fixing of discrete electrode wires, or printed circuit techniques, require a spacing of approximately one order of magnitude more. It has been verified that the higher electrical fields that are obtainable by the described structure allow much higher sensitivity at low relative humidity with a modest applied voltage, than is possible with devices such as those of the Mayer, or Ovshinsky patents or of the surface resistive devices shown in Nicholas et al U.S. Pat. No. 3,916,367. An added benefit of the structure of this invention is that it can be formed at a relatively low cost and that the technology for forming it is substantially established.

What is claimed is:

1. A multi-layered device for sensing humidity comprising a homogeneous porous monolithic dielectric structure, a plurality of electric field-producing electrode layers stacked in planes one above each other which extend substantially entirely across two dimensions of said device and which are buried into said dielectric structure with alternating ones of said electrode layers being connected to separate conductive terminals and with said electrodes being separated by said dielectric structure, which structure is formed with at least a ten percent open cell construction wherein the dielectric is comprised of:

| | |
|---|---|
| Magnesium titanate (MgTiO$_3$) | 65%–75% by weight |
| Zinc oxide (ZnO) | 10%–20% by weight |
| Calcium titanate (CaTiO$_3$) | 4%–7% by weight |
| Titanium dioxide (TiO$_2$) | 6%–9% by weight. |

2. A multi-layered device for sensing humidity comprising a homogeneous porous monolithic dielectric structure, a plurality of electric field-producing electrode layers stacked in planes one above each other which extend substantially entirely across two dimensions of said device and which are buried into said dielectric structure with alternating ones of said electrode layers being connected to separate conductive terminals and with said electrodes being separated by said dielectric structure, which structure is formed with at least a ten percent open cell construction wherein the dielectric is comprised of cerium titanate and the firing temperature ranges from 1120° to 1220° C. with a firing time of approximately 1 hour.

* * * * *